(12) United States Patent
Lin et al.

(10) Patent No.: US 10,703,728 B1
(45) Date of Patent: Jul. 7, 2020

(54) CRYSTALLINE FORM OF OLAPARIB AND A PROCESS FOR PREPARING THE SAME

(71) Applicant: SCINOPHARM TAIWAN, LTD., Tainan (TW)

(72) Inventors: Wen-Wei Lin, Tainan (TW); Tsung-Cheng Hu, Tainan (TW); Yuan-Chang Huang, Tainan (TW); Yung-Hung Chang, Tainan (TW); Kuan-Hsun Wang, Tainan (TW)

(73) Assignee: ScinoPharm Taiwan, Ltd., Shan-Hua, Tainan (TW)

( * ) Notice: Subject to any disclaimer, the term of this patent is extended or adjusted under 35 U.S.C. 154(b) by 0 days.

(21) Appl. No.: 16/444,442

(22) Filed: Jun. 18, 2019

(51) Int. Cl.
*C07D 237/32* (2006.01)

(52) U.S. Cl.
CPC ........ *C07D 237/32* (2013.01); *C07B 2200/13* (2013.01)

(58) Field of Classification Search
CPC ............................ C07D 237/32; C07D 403/10
See application file for complete search history.

(56) References Cited

U.S. PATENT DOCUMENTS

| | | | | |
|---|---|---|---|---|
| 6,894,171 B1 * | 5/2005 | Bauer | ................ | C07D 277/28 548/204 |
| 7,449,464 B2 | 11/2008 | Martin et al. | | |
| 7,692,006 B2 | 4/2010 | Menear et al. | | |
| 8,183,369 B2 | 5/2012 | Quigley et al. | | |
| 8,247,416 B2 | 8/2012 | Menear et al. | | |
| 8,475,842 B2 | 7/2013 | Bechtold et al. | | |
| 9,981,951 B2 | 5/2018 | Novo et al. | | |
| 2005/0222233 A1 * | 10/2005 | Rukhman | ............ | C07D 257/04 514/381 |
| 2015/0284416 A1 | 10/2015 | Zhao et al. | | |
| 2017/0174662 A1 * | 6/2017 | Novo | ................... | C07D 403/10 |
| 2017/0204067 A1 | 7/2017 | Lin | | |

FOREIGN PATENT DOCUMENTS

| | | |
|---|---|---|
| CN | 105439961 A | 3/2016 |
| JP | 2014-206389 A | 10/2014 |
| WO | WO-2008-047082 A2 | 4/2008 |
| WO | WO-2008-047082 A3 | 4/2008 |
| WO | WO-2009-050469 A1 | 4/2009 |
| WO | WO-2017-123156 A1 | 7/2017 |

OTHER PUBLICATIONS

International Search Report and Written Opinion dated Apr. 26, 2017, for PCT Application No. PCT/SG2017/050016, filed Jan. 13, 2017, 16 pages.
United States Patent and Trademark Office, Notice of Allowance for U.S. Appl. No. 15/405,155, dated Oct. 3, 2017, 6 pages.
Kakkar, et al., Isolation and Characterization of Ciprofloxacin-HCL Crystals, 1997, pp. 1063-1067.

* cited by examiner

*Primary Examiner* — Emily A Bernhardt
(74) *Attorney, Agent, or Firm* — Mintz Levin Cohn Ferris Glovsky and Popeo, P.C.

(57) ABSTRACT

In certain aspects, the invention provides a novel crystalline form of olaparib (4-[(3-[(4-cyclopropylcarbonyl)piperazin-4-yl]carbonyl)-4-fluorophenyl]methyl(2H)phthalazin-1-one). In related aspects, the invention provides a processe for preparing the novel crystalline form of olaparib. The process includes forming a solution comprising crude olaparib and an organic solvent; adding the solution to an anti-solvent to form a slurry comprising a precipitate; isolating the precipitate; and drying the precipitate to obtain a crystalline form III of olaparib.

17 Claims, 3 Drawing Sheets

CRYSTALLINE FORM OF OLAPARIB AND A PROCESS FOR PREPARING THE SAME

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Olaparib refers to 4-[(3-[(4-cyclopropylcarbonyl)piperazin-4-yl]carbonyl)-4-fluorophenyl]methyl(2H)phthalazin-1-one having the structure:

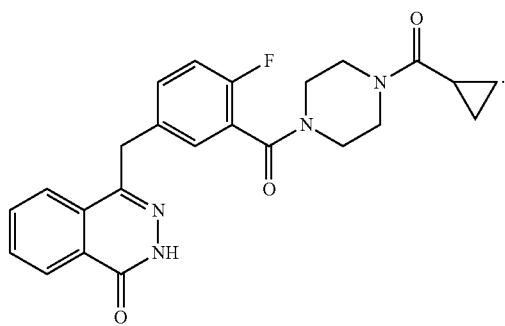 [SMILES: O=C(c1cc(Cc2n[nH]c(=O)c3ccccc23)ccc1F)N1CCN(C(=O)C2CC2)CC1]

Olaparib is a phthalizinone compound developed as a poly(ADP-ribose) polymerase (PARP) inhibitor for use in treating cancers including ovarian, breast, and prostate cancers. Olaparib has been approved by the U.S. Food and Drug Administration for treatment of women with advanced ovarian cancer associated with defective BRCA genes.

Synthesis of olaparib and characterization of solids forms of the compound are disclosed in U.S. Pat. Nos. 8,247,416; 7,692,006; 8,183,369, 9,981,951, and 8,475,842. Specifically, U.S. Pat. No. 8,247,416 discloses 4-[3-(4-cyclopropanecarbonyl-piperazine-1-carbonyl)-4-fluoro-benzyl]-2H-pthalazin-1-one (Compound A) substantially in crystalline form, and in particular in Form A. This patent also discloses a method of synthesizing 4-[3-(4-cyclopropanecarbonyl-piperazine-1-carbonyl)-4-fluoro-benzyl]-2H-pthalazin-1-one from 2-fluoro-5-(4-oxo-3,4-dihydro-phthalazin-1-ylmethyl)-benzoic acid.

U.S. Pat. No. 7,692,006 discloses other methods of obtaining 4-[3-(4-cyclopropanecarbonyl-piperazine-1-carbonyl)-4-fluoro-benzyl]-2H-pthalazin-1-one (Compound A) as crystalline Form A. This patent also discloses an intermediate of 2-fluoro-5-(4-oxo-3,4-dihydro-phthalazin-1-ylmethyl)-benzoic acid (ED) useful for preparing olaparib and a method of synthesizing the intermediate.

U.S. Pat. No. 8,183,369 discloses 4-[3-(4-cyclopropanecarbonyl-piperazine-1-carbonyl)-4-fluoro-benzyl]-2H-pthalazin-1-one as crystalline Form L and a method of obtaining the form from crystalline Form A of 4-[3-(4-cyclopropanecarbonyl-piperazine-1-carbonyl)-4-fluoro-benzyl]-2H-pthalazin-1-one.

U.S. Pat. No. 9,981,951 discloses a solid described as crystalline Form B of olaparib (a hydrated crystalline form).

U.S. Pat. No. 8,475,842, discloses a solid described as crystalline Form H of 4-[3-(4-cyclopropanecarbonyl-piperazine-1-carbonyl)-4-fluoro-benzyl]-2H-pthalazin-1-one (Compound I).

Although the above-mentioned crystalline forms have been disclosed, new solid forms of olaparib are still needed for enhancing the compound's demonstrated efficacy in the treatment of cancers, as well as for improving processes for manufacture of pharmaceutical formulations containing a solid form of olaparib. The present invention meets this need, providing a novel crystalline form of olaparib and a process for preparing the crystalline form.

BRIEF SUMMARY OF THE INVENTION

In a first aspect, the invention provides crystalline form III of olaparib, which is characterized by the X-ray powder diffraction data, thermogravimetric analytical data, and differential scanning calorimetry data described herein.

In a second aspect, the invention provides a process for preparing the crystalline form III of olaparib. The process includes: forming a solution comprising crude olaparib and an organic solvent; adding the solution to an anti-solvent to form a slurry comprising a precipitate; isolating the precipitate; and drying the precipitate to obtain the crystalline form III of olaparib.

DETAILED DESCRIPTION OF THE INVENTION

I. General

Figure 1:
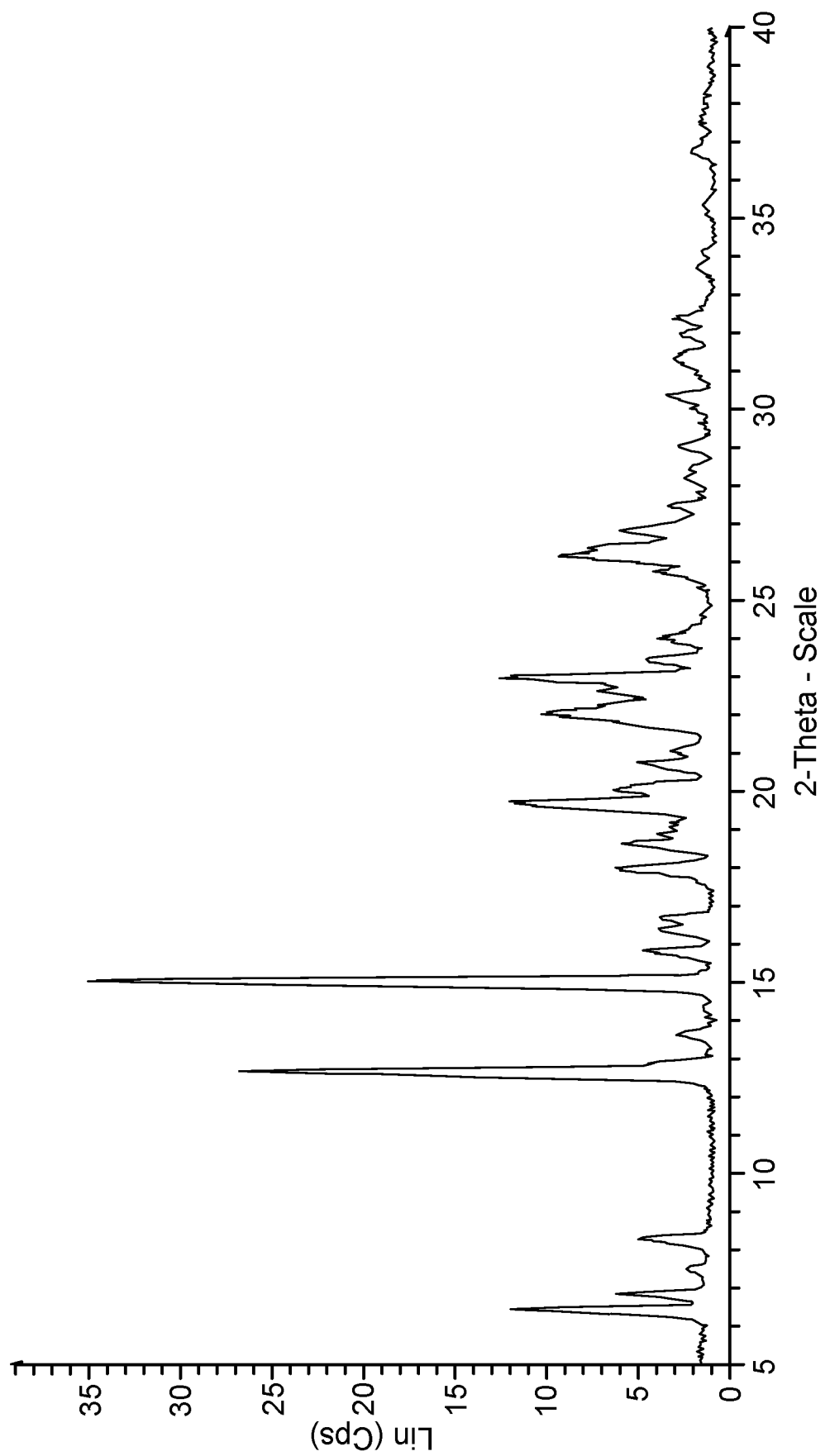
FIG. 1 shows the X-ray powder diffraction (XRPD) pattern recorded for the crystalline form III of olaparib.
Figure 2:
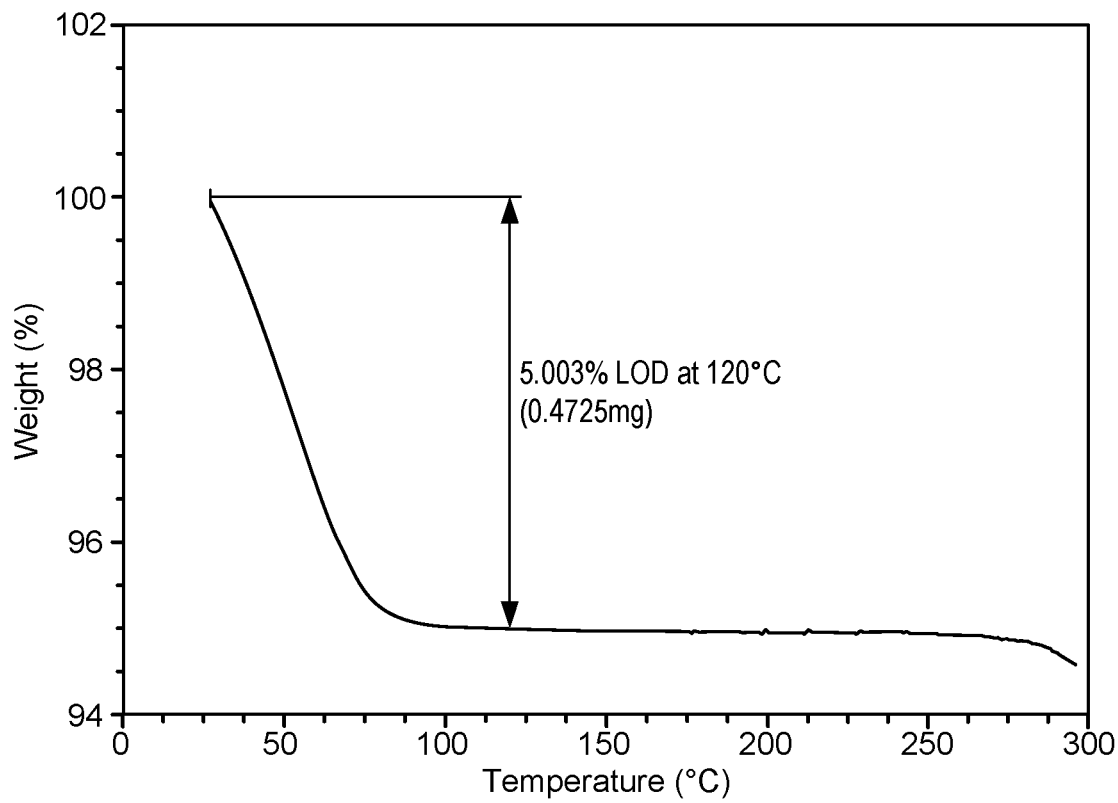
FIG. 2 shows the thermogravimetric analysis (TGA) thermogram recorded for crystalline form III of olaparib

The present invention provides a novel solid form of olaparib characterized by exceptional crystallinity and stability. Among other advantages, the novel solid form can be prepared using a high-yielding process under mild conditions, which is suitable for a large scale production. In addition, the novel solid form can be stored and/or used for manufacture of medicaments without converting to other forms such as non-crystalline forms.

II. Definitions

"Crude" refers to a mixture including a desired compound (e.g., olaparib) and at least one other species (e.g., a solvent, a reagent such as an acid or base, a starting material, or a byproduct of a reaction giving rise to the desired compound).

"Solvent" refers to a liquid substance capable of dissolving olaparib at a concentration of at least about 2.5% (w/w) at 60° C. "Anti-solvent" refers to a liquid substance that does not dissolve olaparib at a concentration of about 2.5% (w/w) at 60° C. More particularly, anti-solvents and solvents suitable for olaparib are shown in the Table and summary below:

| Solubility of olaparib at 60° C. | | | | | | |
|---|---|---|---|---|---|---|
| Toluene | EtOH | ACN | cyclohexane | IPA | THF | EA |
| <16.9 mg/mL <1.9 wt % | 21-23 mg/mL 2.6-2.9 wt % | <16.2 mg/mL <2.1 wt % | <16.2 mg/mL <2.1 wt % | <16.2 mg/mL <2.1 wt % | <16.9 mg/mL <1.9 wt % | <16.2 mg/mL <1.8 wt % |
| DMAc | Pyridine | Xylenes | n-heptane | water | n-butanol | MeOH |
| >220.0 mg/mL >23.5 wt % | >210.0 mg/mL >21.5 wt % | <16.2 mg/mL <1.9 wt % | <16.2 mg/mL <2.4 wt % | <16.2 mg/mL <1.6 wt % | <16.9 mg/mL <2.1 wt % | 53-70 mg/mL 6.7-8.8 wt % |

| Solubility of olaparib at room temperature | |
|---|---|
| AcOH | DMSO |
| >210.0 mg/mL >20.0 wt % | >210.0 mg/mL >19.1 wt % |

| Summary | | |
|---|---|---|
| Solvents for olaparib | | Anti-solvents for olaparib |
| Solubility of olaparib: >15% (w/w) | Solubility of olaparib: 2.5-10% (w/w) | Solubility of olaparib: <2.5% (w/w) |
| AcOH DMSO DMAc Pyridine | EtOH MeOH | Toluene ACN Cyclohexane IPA THF EA Xylenes n-heptane Water n-butanol |

Suitable solvents described herein, refer to solvents characterized with high solubility of olaparib at a concentration of at least about 2.5% (w/w) at 60° C. Anti-solvents, are generally considered 'poor solvents', refer to solvents characterized with low solubility of olaparib at a concentration of less than about 2.5% (w/w) at 60° C. In the Tables above, examples of good solvents include, but are not limited to, an alcohol (e.g., methanol or ethanol), acetic acid, dimethylacetamide, dimethyl sulfoxide and pyridine. Examples of poor solvents (anti-solvents) include, but are not limited to, water, toluene, acetonitrile, cyclohexane, isopropanol, tetrahydrofuran, n-butanol, xylenes, ethyl acetate and n-heptane.

"Alcohol" refers to an alkyl group having a hydroxy group attached to a carbon of the chain, wherein the alkyl group is defined as a straight or branched, saturated, aliphatic radical having the number of carbon atoms indicated (i.e., $C_{1-4}$ means one to four carbons). For example, $C_{1-4}$ alcohol includes methanol, ethanol, n-propanol, isopropanol, n-butanol, sec-butanol, isobutanol, and tert-butanol. Alcohols useful in the present invention are fully saturated. One of skill in the art will appreciate that other alcohols are useful in the present invention.

"PPW" refers to "Purified Process Water".

"Precipitating" refers to the process of causing a compound in a solution to coalesce into a solid form of the substance (i.e., a precipitate). The entirety of a compound in a solution, or any fraction thereof, can be caused to precipitate. The solid form of the substance can be amorphous or crystalline.

"Crystalline form" refers to a solid form of a compound wherein the constituent molecules are packed in a regularly ordered, repeating pattern. A crystalline form can include triclinic, monoclinic, orthorhombic, tetragonal, trigonal, hexagonal, and cubic crystal geometries. A crystalline form can include one or more regions, i.e., grains, with distinct crystal boundaries. A crystalline solid can include two or more crystal geometries.

"Amorphous form" refers to a solid form of a compound having no definite crystal structure, i.e., lacking a regularly ordered, repeating pattern of constituent molecules.

"Isolating" refers to the process of isolating at least a portion of a first substance (e.g., a precipitate) from a mixture including the substance and at least one additional substance. In some instances, the isolated substance is substantially free at least one of the additional substances present in the original mixture.

Figure 4:
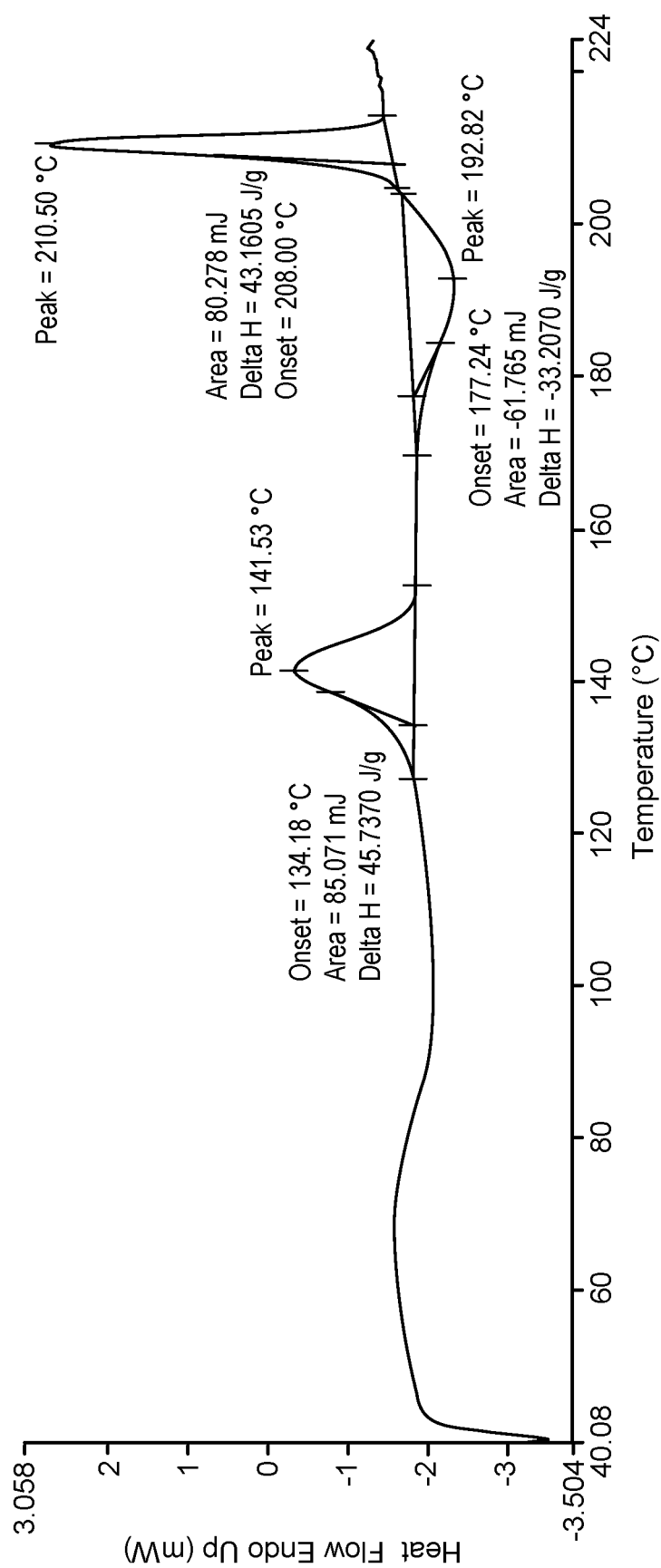
FIG. 4 shows the differential scanning calorimetry (DSC) thermogram recorded for crystalline form B of olaparib in U.S. Pat. No. 9,981,951.

"Substantially free of exothermic peaks", as used herein in a differential scanning calorimetry (DSC) thermogram, refers to the absence of exothermic peak(s) in the DSC thermogram by a visual inspection. The presence of an exothermic peak can be determined by an enthalpy change (ΔH) calculated through the integration of the area under the curve (mJ) (i.e., peak area) over a sample weight (mg). For example, as described in U.S. Pat. No. 9,981,951 (see the DSC thermogram in FIG. 4), the enthalpy change (ΔH) of any exothermic peak at 192.8° C. is about 33.2 J/g. More specifically, the term "Substantially free of exothermic peaks", as used herein in a differential scanning calorimetry (DSC) thermogram, refers to any exothermic peak having an enthalpy change (ΔH) of no more than about 2.0 J/g.

The terms "about" and "around", as used herein to modify a numerical value, indicate a close range around that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

III. Crystalline Form III of Olaparib

In a first aspect, the invention provides a crystalline form III of olaparib. In some embodiments, crystalline form III of olaparib is characterized by an X-ray powder diffraction pattern including one or more peaks (i.e., 1, 2, 3, 4, 5, 6, 7, or 8 peaks) at about 6.4, 6.8, 8.3, 12.7, 15.0, 19.7, 22.0 and 23.0±0.2 degrees two-theta, and further characterized by a differential scanning calorimetry thermogram, wherein the differential scanning calorimetry thermogram is substantially free of exothermic peaks between 50° C. to 250° C. in the heating process. In some embodiments, the X-ray powder diffraction pattern further comprises one or more peaks (i.e., 1, 2, 3, 4, 5, 6, 7, 8, 9, or 10 peaks) at about 7.5, 13.6, 15.8, 16.4, 16.7, 18.0, 18.6, 23.5, 26.2 and 26.8±0.2 degrees two-theta.

In some embodiments, crystalline form III of olaparib is characterized by an X-ray powder diffraction pattern including peaks at about 6.4, 6.8, 8.3, 12.7, 15.0, 19.7, 22.0 and 23.0±0.2 degrees two-theta, and further characterized by a differential scanning calorimetry thermogram, wherein the differential scanning calorimetry thermogram is substantially free of exothermic peaks between 50° C. to 250° C. in the heating process. In some embodiments, the X-ray powder diffraction pattern further comprises peaks at about 7.5, 13.6, 15.8, 16.4, 16.7, 18.0, 18.6, 23.5, 26.2 and 26.8±0.2 degrees two-theta.

In some embodiments, crystalline form III of olaparib is characterized by an X-ray powder diffraction pattern including peaks at about 6.4, 6.8, 7.5, 8.3 12.7, 13.6, 15.0, 15.8, 16.4, 16.7, 18.0, 18.6, 19.7, 22.0, 23.0, 23.5, 26.2 and 26.8±0.2 degrees two-theta, and further characterized by a differential scanning calorimetry thermogram, wherein the differential scanning calorimetry thermogram is substantially free of exothermic peaks between 50° C. to 250° C. in the heating process.

In some embodiments, crystalline form III of olaparib is characterized by an X-ray powder diffraction pattern substantially in accordance with FIG. 1.

Methods for collection of XRPD data are known in the art, and any such methods can be used for characterizing the crystalline form III of olaparib. For example, the X-ray powder diffraction patterns described herein can be generated using Cu Kα1 radiation.

In some embodiments, crystalline form III of olaparib is characterized by a weight loss at about 5% to about 6% upon heating at around 120° C., as measured by thermal gravimetric analysis. In some embodiments, the weight loss is measured using a sample weighting around 15-20 mg, which is subject to temperature ranging from 30° C. to 300° C. using a ramp of 10° C./min.

In some embodiments, crystalline form III of olaparib is characterized by a differential scanning calorimetry thermogram comprising one or more endothermic peaks (i.e., 1, 2 or 3 endothermic peaks) at around 72.0, 144.6 and 212.5° C. In some embodiments, the differential scanning calorimetry thermogram comprises endothermic peaks at around 72.0, 144.6 and 212.5° C. In some embodiments, the differential scanning calorimetry thermogram comprises endothermic peaks; and is substantially free of exothermic peaks between 50° C. to 250° C. in the heating process. In some embodiments, the differential scanning calorimetry thermogram comprises endothermic peaks at around 72.0, 144.6 and 212.5° C.; and is substantially free of exothermic peaks between 50° C. to 250° C. in the heating process.

In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g.

Figure 3:
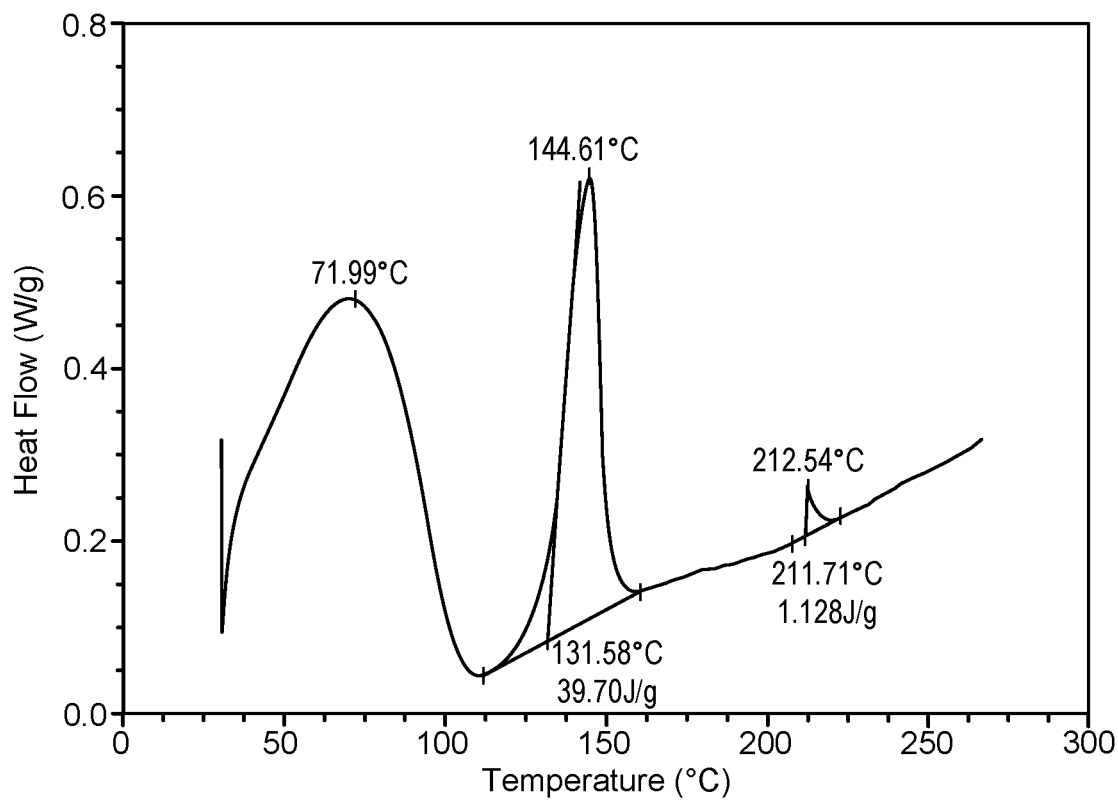
FIG. 3 shows the differential scanning calorimetry (DSC) thermogram recorded for crystalline form III of olaparib

In some embodiments, crystalline form III of olaparib is characterized by a differential scanning calorimetry thermogram substantially in accordance with FIG. 3. In some embodiments, a thermogram is recorded using a sample weight around 2-5 mg, which is subjected to temperatures ranging from 30° C. to 270° C. using a ramp of 10° C./min.

In some embodiments, crystalline form III of olaparib is characterized by an X-ray powder diffraction pattern including one or more peaks (i.e., 1, 2, 3, 4, 5, 6, 7, or 8 peaks) at about 6.4, 6.8, 8.3, 12.7, 15.0, 19.7, 22.0 and 23.0±0.2 degrees two-theta; and is further characterized by a differential scanning calorimetry thermogram, wherein the differential scanning calorimetry thermogram is substantially free of exothermic peaks between 50° C. to 250° C. in the heating process. In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g. In some embodiments, the X-ray powder diffraction pattern further comprises one or more peaks (i.e., 1, 2, 3, 4, 5, 6, 7, 8, 9, or 10 peaks) at about 7.5, 13.6, 15.8, 16.4, 16.7, 18.0, 18.6, 23.5, 26.2 and 26.8±0.2 degrees two-theta.

In some embodiments, crystalline form III of olaparib is characterized by an X-ray powder diffraction pattern including peaks at about 6.4, 6.8, 8.3, 12.7, 15.0, 19.7, 22.0 and 23.0±0.2 degrees two-theta; and is further characterized by a differential scanning calorimetry thermogram, wherein the differential scanning calorimetry thermogram is substantially free of exothermic peaks between 50° C. to 250° C. in the heating process. In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g. In some embodiments, the X-ray powder diffraction pattern further comprises peaks at about 7.5, 13.6, 15.8, 16.4, 16.7, 18.0, 18.6, 23.5, 26.2 and 26.8±0.2 degrees two-theta.

In some embodiments, crystalline form III of olaparib is characterized by an X-ray powder diffraction pattern including peaks at about 6.4, 6.8, 7.5, 8.3 12.7, 13.6, 15.0, 15.8, 16.4, 16.7, 18.0, 18.6, 19.7, 22.0, 23.0, 23.5, 26.2 and 26.8±0.2 degrees two-theta; and is further characterized by a differential scanning calorimetry thermogram, wherein the differential scanning calorimetry thermogram is substantially free of exothermic peaks between 50° C. to 250° C. in the heating process. In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g.

In some embodiments, crystalline form III of olaparib is characterized by an X-ray powder diffraction pattern including one or more peaks (i.e., 1, 2, 3, 4, 5, 6, 7, or 8 peaks) at about 6.4, 6.8, 8.3, 12.7, 15.0, 19.7, 22.0 and 23.0±0.2 degrees two-theta; and is further characterized by a differential scanning calorimetry thermogram, wherein the differential scanning calorimetry thermogram comprises endothermic peaks; and is substantially free of exothermic peaks between 50° C. to 250° C. in the heating process. In some embodiments, crystalline form III of olaparib is characterized by an X-ray powder diffraction pattern including one or more peaks (i.e., 1, 2, 3, 4, 5, 6, 7, or 8 peaks) at about 6.4, 6.8, 8.3, 12.7, 15.0, 19.7, 22.0 and 23.0±0.2 degrees two-theta; and is further characterized by a differential scanning calorimetry thermogram, wherein the differential scanning calorimetry thermogram comprises endothermic peaks at around 72.0, 144.6 and 212.5° C.; and is substantially free of exothermic peaks between 50° C. to 250° C. in the heating process. In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g. In some embodiments, the X-ray powder diffraction pattern further comprises one or more peaks (i.e., 1, 2, 3, 4, 5, 6, 7, 8, 9, or 10 peaks) at about 7.5, 13.6, 15.8, 16.4, 16.7, 18.0, 18.6, 23.5, 26.2 and 26.8±0.2 degrees two-theta.

In some embodiments, crystalline form III of olaparib is characterized by an X-ray powder diffraction pattern including peaks at about 6.4, 6.8, 8.3, 12.7, 15.0, 19.7, 22.0 and 23.0±0.2 degrees two-theta; and is further characterized by a differential scanning calorimetry thermogram, wherein the differential scanning calorimetry thermogram comprises endothermic peaks; and is substantially free of exothermic peaks between 50° C. to 250° C. in the heating process. In some embodiments, crystalline form III of olaparib is characterized by an X-ray powder diffraction pattern including peaks at about 6.4, 6.8, 8.3, 12.7, 15.0, 19.7, 22.0 and 23.0±0.2 degrees two-theta; and is further characterized by a differential scanning calorimetry thermogram, wherein the differential scanning calorimetry thermogram comprises endothermic peaks at around 72.0, 144.6 and 212.5° C.; and is substantially free of exothermic peaks between 50° C. to 250° C. in the heating process. In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g. In some embodiments, the X-ray powder diffraction pattern further comprises peaks at about 7.5, 13.6, 15.8, 16.4, 16.7, 18.0, 18.6, 23.5, 26.2 and 26.8±0.2 degrees two-theta.

In some embodiments, crystalline form III of olaparib is characterized by an X-ray powder diffraction pattern including peaks at about 6.4, 6.8, 7.5, 8.3 12.7, 13.6, 15.0, 15.8, 16.4, 16.7, 18.0, 18.6, 19.7, 22.0, 23.0, 23.5, 26.2 and 26.8±0.2 degrees two-theta; and is further characterized by a differential scanning calorimetry thermogram, wherein the differential scanning calorimetry thermogram comprises endothermic peaks and is substantially free of exothermic peaks between 50° C. to 250° C. in the heating process. In some embodiments, crystalline form III of olaparib is characterized by an X-ray powder diffraction pattern including peaks at about 6.4, 6.8, 7.5, 8.3 12.7, 13.6, 15.0, 15.8, 16.4, 16.7, 18.0, 18.6, 19.7, 22.0, 23.0, 23.5, 26.2 and 26.8±0.2 degrees two-theta; and is further characterized by a differential scanning calorimetry thermogram, wherein the differential scanning calorimetry thermogram comprises endothermic peaks at around 72.0, 144.6 and 212.5° C.; and is substantially free of exothermic peaks between 50° C. to 250° C. in the heating process. In some embodiments, the substantially free of exothermic peaks in the differential scanning calorimetry thermogram is determined by a visual inspection, wherein exothermic peaks are absent. In some embodiments, the substantially free of exothermic peaks in the differential scanning calorimetry thermogram is determined by an enthalpy change (ΔH) of an exothermic peak, wherein the enthalpy change (ΔH) of any exothermic peak is no more than about 2.0 J/g. In some embodiments, the enthalpy change (ΔH) of any exothermic peak is no more than about 1.0 J/g, about 0.5 J/g, about 0.2 J/g, or about 0.1 J/g. In some embodiments, the enthalpy change (ΔH) of any exothermic peak is from about 2.0 J/g to about 1.0 J/g, from about 1.0 J/g to about 0.5 J/g, from about 0.5 J/g to about 0.2 J/g, from about 0.2 J/g to about 0.1 J/g, from about 0.1 J/g to about 0.05 J/g, or near zero J/g. In some embodiments, the enthalpy change (ΔH) of any exothermic peak is near zero J/g.

In some embodiments, crystalline form III of olaparib is characterized by an X-ray powder diffraction pattern substantially in accordance with FIG. 1; and is further characterized by a differential scanning calorimetry thermogram substantially in accordance with FIG. 3.

In some embodiments, the crystalline form III of olaparib is a hydrated form. In some embodiments, the hydrated form includes about 5% to about 6% (w/w) of water.

IV. A Process for Preparing Crystalline Form III of Olaparib

In a second aspect, the invention provides a process for preparing crystalline form III of olaparib. The process includes:

a) forming a solution including crude olaparib and an organic solvent;

b) adding the solution to an anti-solvent to form a slurry solution including a precipitate;

c) isolating the precipitate; and d) drying the precipitate to obtain the crystalline form III of olaparib.

In general, the crude olaparib used in the methods of the invention can include olaparib and at least one other substance associated with the synthesis and/or purification of the olaparib (e.g., a solvent; a starting material or intermediate; a reagent such as an acid or base; or a combination thereof). In general, the crude olaparib can include at least 50% (w/w) olaparib. The crude olaparib can include, for example, from about 50% (w/w) to about 55% (w/w) olaparib, from about 55% (w/w) to about 60% (w/w) olaparib, from about 60% (w/w) to about 65% (w/w) olaparib, from about 65% (w/w) to about 70% (w/w) olaparib, from about 70% (w/w) to about 75% (w/w) olaparib, from about 75% (w/w) to about 80% (w/w) olaparib, from about 80% (w/w) to about 85% (w/w) olaparib, from about 85% (w/w) to about 90% (w/w) olaparib, from about 90% (w/w) to about 95% (w/w) olaparib, or from about 95% (w/w) to about 99% (w/w) olaparib. In some embodiments, the crude olaparib includes from about 50% (w/w) to about 99% (w/w) olaparib, from about 55% (w/w) to about 95% (w/w) olaparib, from about 60% (w/w) to about 90% (w/w) olaparib, from about 65% (w/w) to about 85% (w/w) olaparib, or from about 70% (w/w) to about 80% (w/w) olaparib. The crude olaparib can be obtained in a number of forms prior to dissolution according to the methods of the invention. For example, the crude compound can be a crystalline form, an amorphous form, a glass, or a foam.

Any solvent suitable for dissolving the crude olaparib can be used for forming the solution in the process of the invention. In some embodiments, the organic solvent includes a $C_{1-4}$ alcohol. In some embodiments, the organic solvent is methanol, ethanol, n-propanol, isopropanol, n-butanol, sec-butanol, isobutanol, tert-butanol, or combinations thereof. In some embodiments, the organic solvent includes methanol. In some embodiments, the organic solvent is methanol.

Any amount of solvent suitable for dissolving the crude olaparib can be used for forming the solution. In general, the solvent can be used in amounts such that the solution can include the crude olaparib in an amount of at least around 1% (w/w). In some embodiments, the solution includes the crude olaparib in an amount ranging from about 1% (w/w) to about 25% (w/w). The solution can include, for example, the crude olaparib in an amount ranging from about 1% (w/w) to about 10% (w/w), from about 5% (w/w) to about 10% (w/w), from about 10% (w/w) to about 15% (w/w), from about 15% (w/w) to about 20% (w/w), or from about 20% (w/w) to about 25% (w/w). In some embodiments, the solution includes the crude olaparib in an amount ranging from about 1% (w/w) to about 10% (w/w). In some embodiments, the solution includes the crude olaparib in an amount ranging from about 1% (w/w) to about 10% (w/w), from about 3% (w/w) to about 10% (w/w), from about 4% (w/w) to about 10% (w/w), from about 4% (w/w) to about 8% (w/w), or from about 4% (w/w) to about 7% (w/w). In some embodiments, the solution includes the crude olaparib in an amount of about 5% (w/w).

In some embodiments, the solution further includes the anti-solvent. In some embodiments, the solution further includes water. In general, water can be used in amounts such that the solution can include water in an amount of at least around 10% (w/w). In some embodiments, the solution includes water in an amount ranging from about 10% (w/w) to about 30% (w/w). The solution can include, for example, water in an amount ranging from about 10% (w/w) to about 15% (w/w), from about 15% (w/w) to about 20% (w/w), from about 20% (w/w) to about 25% (w/w), or from about 25% (w/w) to about 30% (w/w). In some embodiments, the solution includes water in an amount ranging from about 10% (w/w) to about 15% (w/w), from about 15% (w/w) to about 20% (w/w), or from about 20% (w/w) to about 25% (w/w). In some embodiments, the solution includes water in an amount ranging from about 20% (w/w) to about 25% (w/w). In some embodiments, the solution includes water in an amount of about 23% (w/w).

In some embodiments, the solution includes a $C_{1-4}$ alcohol and the crude olaparib in the solution in an amount ranging from about 1% (w/w) to about 25% (w/w). In some embodiments, the solution includes methanol and the crude olaparib in an amount ranging from about 1% (w/w) to about 10% (w/w). In some embodiments, the solution includes methanol, water, and the crude olaparib, wherein methanol and water has a ratio of about 4:1 (v/v) and the crude olaparib is present in an amount ranging from about 1% (w/w) to about 10% (w/w). In some embodiments, the solution includes methanol, water, and the crude olaparib, wherein methanol and water has a ratio of about 4:1 (v/v) and the crude olaparib is present in an amount ranging from about 4% (w/w) to about 7% (w/w). In some embodiments, the solution includes methanol, water, and the crude olaparib, wherein methanol and water has a ratio of about 4:1 (v/v) and the crude olaparib is present in an amount of about 5% (w/w).

In some embodiments, forming the solution (i.e., step a)) includes heating the solution. In some embodiments, the solution is heated to a temperature of at least about 50° C. The solution can be heated, for example, at a temperature ranging from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., from about 85° C. to about 90° C., from about 90° C. to about 95° C., or from about 95° C. to about 100° C. In some embodiments, the solution is heated at a temperature ranging from about 50° C. to about 100° C., from about 55° C. to about 95° C., from about 60° C. to about 90° C., from about 65° C. to about 85° C., or from about 70° C. to about 80° C. In some embodiments, forming the solution comprises heating the solution to a temperature ranging from about 55° C. to about 65° C.

One of skill in the art will appreciate that the heating temperature will depend, in part, on one or more factors including the particular organic solvent, the quantity of the solvent, and the level of purity of the crude olaparib. Such factors will also determine, to an extent, the length of time required to dissolve the crude compound. Any suitable length of the time can be used, ranging from a few minutes to several hours. For example, the mixture including the crude olaparib and the organic solvent can be mixed, with or without heating, for about 10 minutes, or about 20 minutes, or 30 minutes, or about 40 minutes, or about 1 hour.

In general, step b) is performed by adding the solution formed from step a) to an anti-solvent to form a slurry solution including a precipitate.

Any liquid substance suitable for precipitating olaparib can be used as the anti-solvent in the process for preparing olaparib as crystalline Form III. In some embodiments, the anti-solvent includes water. In some embodiments, the anti-solvent is water. Any amount of the anti-solvent can be used for forming the slurry. In general, the anti-solvent can be used in an amount such that the slurry comprises at least about 10% (w/w) anti-solvent. In some embodiments, the slurry includes the anti-solvent in an amount ranging from about 10% (w/w) to about 40% (w/w), from about 10% (w/w) to about 35% (w/w), from about 10% (w/w) to about 30% (w/w), from about 20% (w/w) to about 40% (w/w), from about 20% (w/w) to about 35% (w/w), from about 25% (w/w) to about 40% (w/w), from about 25% (w/w) to about 35% (w/w), from about 30% (w/w) to about 40% (w/w), or from about 30% (w/w) to about 35% (w/w). In some embodiments, the slurry includes the anti-solvent in an amount ranging from about 20% (w/w) to about 40% (w/w), from about 20% (w/w) to about 35% (w/w), from about 25% (w/w) to about 40% (w/w), from about 25% (w/w) to about 35% (w/w), from about 30% (w/w) to about 40% (w/w), or from about 30% (w/w) to about 35% (w/w). In some embodiments, the slurry includes the anti-solvent in an amount ranging from about 25% (w/w) to about 40% (w/w), from about 25% (w/w) to about 35% (w/w), from about 30% (w/w) to about 40% (w/w), or from about 30% (w/w) to about 35% (w/w). In some embodiments, the slurry includes the anti-solvent in an amount of about 30% (w/w). In some embodiments, the slurry includes the anti-solvent in an amount of about 35% (w/w).

In some embodiments, the slurry includes a $C_{1-4}$ alcohol; olaparib in an amount ranging from about 1% (w/w) to about 25% (w/w); and water in an amount ranging from about 25% (w/w) to about 40% (w/w). In some embodiments, the slurry includes methanol; olaparib in an amount ranging from about 1% (w/w) to about 10% (w/w); and water in an amount ranging from about 25% (w/w) to about 40% (w/w). In some embodiments, the slurry includes methanol; olaparib in an amount ranging from about 1% (w/w) to about 10% (w/w); and water in an amount ranging from about 25% (w/w) to about 35% (w/w). In some embodiments, the slurry includes methanol, water, and olaparib; wherein methanol and water has a ratio of about 2:1 (v/v) and olaparib is present in an amount ranging from about 1% (w/w) to about 10% (w/w). In some embodiments, the slurry includes methanol, water, and olaparib; wherein methanol and water has a ratio of about 2:1 (v/v) and olaparib is present in an amount ranging from about 4% (w/w) to about 7% (w/w). In some embodiments, the slurry includes methanol, water, and olaparib; wherein methanol and water has a ratio of about 2:1 (v/v) and olaparib is present in an amount of about 5% (w/w).

In some embodiments, the anti-solvent includes a seed of olaparib. In some embodiments, prior to step b), the method further includes adding a seed of olaparib into the anti-solvent. In some embodiments, step b) of the method includes adding the solution to the anti-solvent comprising a seed of olaparib to form a slurry solution including a precipitate. In some embodiments, water in step b) includes a seed of olaparib. In some embodiments, step b) of the method includes adding the solution to water comprising a seed of olaparib to form a slurry solution including a precipitate.

In some embodiments, prior to the isolating the precipitate (i.e., step c)), the method further includes exchanging a solvent of the slurry by removing the solvent including the organic solvent in the slurry and adding the additional anti-solvent into the slurry. In some embodiments, removing the solvent including the organic solvent in the slurry is performed under vacuum. In some embodiments, removing the solvent including the organic solvent in the slurry is performed under vacuum at a temperature of no more than 40° C. In some embodiments, prior to the isolating the precipitate (i.e., step c)), the method further includes exchanging a solvent of the slurry by removing the solvent including methanol in the slurry and adding additional water into the slurry. In some embodiments, removing the solvent including methanol in the slurry is performed under vacuum. In some embodiments, removing the solvent including methanol in the slurry is performed under vacuum at a temperature of no more than 40° C.

In some embodiments, the method further includes cooling the slurry and/or adding a seed of olaparib into the slurry prior to isolating the precipitate. In some embodiments, the method further includes cooling the slurry prior to isolating the precipitate (i.e., step c)). Typically, the slurry can be cooled to a temperature below 30° C. In some embodiments, the slurry can be cooled to a temperature of from about 10° C. to about 30° C. The slurry can be cooled, for example, to a temperature around 25° C., around 20° C., or around 4° C. One of skill in the art will appreciate that the cooling temperature can depend, in part, on the solubility of the olaparib in the solvent/anti-solvent mixture, as well as the quantities of the solvent and anti-solvent used in the process. The cooling can be conducted over any suitable length of time, typically ranging from a few minutes to several hours.

Isolating the precipitated olaparib from the solvent/anti-solvent mixture can be accomplished after slurry formation by a number of techniques, including passing the mixture through a filter to isolate the solid material, centrifuging the mixture, or removing the solvent/anti-solvent supernatant. Alternatively, the slurry can be frozen and the solvent/anti-solvent mixture can be removed from the precipitate via sublimation. In some embodiments, the precipitate of olaparib is isolated from the suspension by filtration. In some embodiments, the process further includes washing the isolated precipitate. Washing can be conducted by triturating the precipitate with additional portions of the anti-solvent or a solvent/anti-solvent mixture. The washing can remove residual impurities, if present. In some embodiments, the process for preparing olaparib as crystalline form III includes washing the isolated precipitate with one or more portions of water or one or more portions of a water/methanol solution.

After isolating the precipitated olaparib, with or without additional washing steps, the olaparib is dried to remove solvent and anti-solvent from the solid material. Drying can be conducted under ambient temperature and pressure. Evaporation of solvent and anti-solvent can be promoted by contacting the solid material with a stream of air, nitrogen, argon, or other another gas or gas mixture. In some embodiments, the precipitate of olaparib is dried with nitrogen purging at room temperature for a time period. In some embodiments, the precipitate is dried under reduced pressure. In some embodiments, the precipitate is dried under reduced pressure and elevated temperatures. In some embodiments, drying the precipitate comprises heating the precipitate to a temperature ranging from about 30° C. to about 80° C. In some embodiments, drying the precipitate comprises heating the precipitate to a temperature ranging from about 30° C. to about 50° C. In some embodiments, drying the precipitate comprises heating the precipitate to a temperature of about 40° C. Any suitable pressure, temperature, and drying time can be used to partially or fully remove the solvent and the anti-solvent from the precipitated olaparib. Drying can be conducted, for example, under reduced pressure and elevated temperature until the weight of the olaparib remains constant.

In some embodiments, the process for preparing the crystalline form III of olaparib comprises:

a) forming a solution including crude olaparib and methanol;

b) adding the solution to water to form a slurry solution including a precipitate;

c) isolating the precipitate; and d) drying the precipitate to obtain the crystalline form III of olaparib.

In some embodiments, the solution further includes water. In some embodiments, the solution includes methanol, water, and the crude olaparib, wherein methanol and water has a ratio of about 4:1 (v/v) and the crude olaparib is present in an amount ranging from about 1% (w/w) to about 10% (w/w). In some embodiments, the solution includes methanol, water, and the crude olaparib, wherein methanol and water has a ratio of about 4:1 (v/v) and the crude olaparib is present in an amount ranging from about 4% (w/w) to about 7% (w/w). In some embodiments, the solution includes methanol, water, and the crude olaparib, wherein methanol and water has a ratio of about 4:1 (v/v) and the crude olaparib is present in an amount of about 5% (w/w).

In some embodiments, water in step b) includes a seed of olaparib. In some embodiments, step b) of the method includes adding the solution to water comprising a seed of olaparib to form a slurry solution including a precipitate.

In some embodiments, the slurry includes methanol, water, and olaparib; wherein methanol and water has a ratio of about 2:1 (v/v) and olaparib is present in an amount ranging from about 1% (w/w) to about 10% (w/w). In some embodiments, the slurry includes methanol, water, and olaparib; wherein methanol and water has a ratio of about 2:1 (v/v) and olaparib is present in an amount ranging from about 4% (w/w) to about 7% (w/w). In some embodiments, the slurry includes methanol, water, and olaparib; wherein methanol and water has a ratio of about 2:1 (v/v) and olaparib is present in an amount of about 5% (w/w).

In some embodiments, prior to the isolating the precipitate (i.e., step c)), the method further includes exchanging a solvent of the slurry by removing the solvent including methanol in the slurry and adding additional water into the slurry. In some embodiments, removing the solvent including methanol in the slurry is performed under vacuum. In some embodiments, removing the solvent including methanol in the slurry is performed under vacuum at a temperature of no more than 40° C.

In some embodiments, the method further includes cooling the slurry prior to isolating the precipitate. In some embodiments, the slurry can be cooled to a temperature of from 15° C. to 25° C.

In some embodiments, the precipitate of olaparib is isolated from the suspension by filtration.

In some embodiments, the precipitate of olaparib is dried with nitrogen purging at room temperature for a time period. In some embodiments, the precipitate is dried under reduced pressure. In some embodiments, the precipitate is dried at a temperature of about 40° C.

V. Examples

The following examples describe methods for characterizing crystalline form III of olaparib and a process for preparing crystalline form III of olaparib suitable for either a laboratory-scale or an industrial scale.

Example 1: Methods for Characterizing Crystalline Form III of Olaparib

X-RAY POWDER DIFFRACTION. X-ray Powder Diffraction patterns were collected on a Bruker AXS D8 Advance diffractometer using Cu Kα1 radiation (40 kV, 40 mA), a 0-2θ goniometer, and divergence of 10 mm slits, a Ge monochromator, and LynxEye detector. The representative XRPD pattern was collected under ambient condition. The scanning parameters included an angular range of 5-40°, a step size of 0.02°, and a scan speed of 0.6 sec/step.

THERMAL GRAVIMETRIC ANALYSIS (TGA). TGA data was collected on a TA Instrument Q500 TGA. Each sample (15-20 mg) was loaded onto a pre-tared platinum crucible and the balance and furnace were purged with nitrogen prior to the analysis with a flow rate set as 40±5 and 60±5 mL/min, respectively. The heating process was programmed to start from 30° C. and stop at 300° C. with a 10° C./min ramp.

DIFFERENTIAL SCANNING CALORIMETRY (DSC). DSC data was collected on a TA Instrument MDSC Q200. Each sample (2-5 mg) was loaded onto a hermetic pan and the analysis was carried out under a constant flow of nitrogen (60 mL/min). The heating process was programmed to start from 30° C. and stop at 270° C. with a 10° C./min ramp.

Example 2: Preparation of the Crystalline Form III of Olaparib

To a 4-neck 2 L flask equipped with an overhead stirrer, thermometer and $N_2$ inlet, crude olaparib (55.00 g), MeOH (1056 mL), and PPW (264 mL) were added. The resulting mixture was heated to a temperature of no less than 55° C. After the solids were dissolved, the resulting solution was filtered through a Buchner funnel to remove foreign particles.

MeOH/PPW (55 mL, v/v=4/1) was added to rinse. And then the solution was cooled to about 35° C. Separetely, a seed of olaparib (1.10 g, form III) and PPW (275 mL) were added to a 4-neck 5 L flask equipped with overhead stirrer, thermometer, and $N_2$ inlet. The above prepared clear solution was added slowly to the 5 L flask over a period of 100 minutes at room temperature. The resulting slurry was distilled at a temperature of no more than 40° C. under vacuum to remove distillate (610 mL), followed by addition of PPW (610 mL). The slurry was cooled to room temperature and then stirred for 1 hour. After stirring, the slurry was filtered through a Buchner funnel to afford a wet cake. The wet cake was washed with MeOH/PPW (165 mL, v/v=½) and then dried at 40° C. to afford Olaparib (52.23 g, 94.96% Yield).

Example 3: Preparation of the Crystalline Form III of Olaparib

To a first reactor, crude olaparib (1.056 Kg), MeOH (16 Kg), and PPW (5.06 Kg) were added. The resulting mixture was heated to 57.7° C. After the solids were dissolved, the resulting solution was filtered through an in-line filter to remove foreign particles. MeOH/PPW (0.88 Kg, v/v=4/1) was added to rinse. And then the solution was cooled to about 35° C. Separately, a seed of olaparib (21.0 g, form III) and PPW (5.27 Kg) were added to a second reactor. The above prepared clear solution was added slowly to the second reactor over a period of 100 minutes at room temperature. The resulting slurry was distilled at a temperature of no more than 40° C. under vacuum to remove distillate (14 L), followed by addition of PPW (14 L). The slurry was cooled to room temperature and then stirred for 1 hour. After stirring, the slurry was filtered to afford a wet cake. The wet cake was washed with MeOH/PPW (8.82 Kg, v/v=½) and then dried at 40° C. to afford Olaparib (0.919 Kg, 95.9% Yield).

Example 4: Preparation of the Crystalline Form III of Olaparib

To a first reactor, crude olaparib (4.196 Kg), MeOH (64.6 Kg), and PPW (20.1 Kg) were added. The resulting mixture was heated to 58° C. After the solids were dissolved, the resulting solution was filtered through an in-line filter to remove foreign particles. MeOH/PPW (3.34 Kg, v/v=4/1) was added to rinse. And then the solution was cooled to about 35° C. Separately, a seed of olaparib (84 g, form III) and PPW (21 Kg) were added to a second reactor. The above prepared clear solution was added slowly to the second reactor over a period of 90 minutes at room temperature. The resulting slurry was solvent-swapped by PPW (82 Kg) at a temperature of no more than 40° C. under vacuum. The slurry was cooled to room temperature and then stirred for 2 hours. After stirring, the slurry was filtered to afford a wet cake. The wet cake was washed with MeOH/PPW (23.6 Kg, v/v=½) and then dried at 40° C. to afford Olaparib (3.683 Kg, 86% Yield).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. Crystalline form III of olaparib, characterized by an X-ray powder diffraction pattern comprising peaks at 6.4, 6.8, 8.3 12.7, 15.0, 19.7, 22.0 and 23.0 degrees 2θ(±0.2 degrees 2θ); and further characterized by a differential scanning calorimetry thermogram, wherein the differential scanning calorimetry thermogram is substantially free of exothermic peaks between 50° C. to 250° C. in the heating process and comprises endothermic peaks at about 72.0, 144.6, and 212.5° C.

2. The crystalline form III of olaparib according to claim 1, wherein the X-ray powder diffraction pattern further comprises peaks at 7.5, 13.6, 15.8, 16.4, 16.7, 18.0, 18.6, 23.5, 26.2 and 26.8±0.2 degrees two-theta.

3. The crystalline form III of olaparib according to claim 1, wherein the X-ray powder diffraction pattern is substantially in accordance with FIG. 1.

4. The crystalline form III of olaparib according to claim 1, further characterized by a weight loss at about 5% to about 6% upon heating at around 120° C., as measured by thermal gravimetric analysis.

5. The crystalline form III of olaparib according to claim 1, wherein the differential scanning calorimetry thermogram is substantially in accordance with FIG. 3.

6. The crystalline form III of olaparib according to claim 3, further characterized by a differential scanning calorimetry thermogram substantially in accordance with FIG. 3.

7. A process for preparing the crystalline form III of olaparib of claim 1, comprising:
   a) forming a solution comprising crude olaparib, an organic solvent, and an anti-solvent;
   b) adding the solution to the anti-solvent to form a slurry solution comprising a precipitate;
   c) isolating the precipitate; and
   d) drying the precipitate to obtain the crystalline form III of olaparib,
wherein the organic solvent is a $C_{1-4}$ alcohol; and the anti-solvent is water.

8. The process of claim 7, wherein forming the solution comprises heating the solution.

9. The process of claim 8, wherein the solution is heated to a temperature ranging from about 55° C. to about 65° C.

10. The process of claim 8, prior to step b), further comprising adding a seed of olaparib into the anti-solvent.

11. The process of claim 8, prior to step c), further comprising exchanging a solvent in the slurry by removing the solvent comprising the organic solvent and adding the anti-solvent.

12. The process of claim 11, further comprising cooling the slurry.

13. The process of claim 12, wherein the slurry is cooled to a temperature ranging from about 10° C. to about 30° C.

14. The process of claim 7, wherein the organic solvent is methanol.

15. The process of claim 8, wherein the solution comprises the crude olaparib in an amount ranging from about 1% (w/w) to 10% (w/w).

16. The process of claim 8, wherein the slurry comprises the anti-solvent in an amount ranging from about 10% (w/w) to 40% (w/w).

17. The process of claim 8, wherein drying the precipitate comprises heating precipitate to a temperature ranging from about 40° C. to about 70° C.

* * * * *